United States Patent
Sarabi et al.

(10) Patent No.: US 6,687,624 B2
(45) Date of Patent: Feb. 3, 2004

(54) METHOD AND COMPUTER SYSTEM FOR ESTABLISHING A RELATIONSHIP BETWEEN A STRESS AND A STRAIN

(75) Inventors: Bahman Sarabi, Krefeld (DE); Martin Wanders, Odenthal (DE); Dietmar Wächtler, Wermelskirchen (DE); Andreas Wende, Mettmann (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/108,150

(22) Filed: Mar. 27, 2002

(65) Prior Publication Data

US 2002/0178832 A1 Dec. 5, 2002

(30) Foreign Application Priority Data

Apr. 4, 2001 (DE) .......................................... 101 16 772

(51) Int. Cl.⁷ .............................. G01L 1/00; G02B 6/00
(52) U.S. Cl. .................... 702/42; 385/128; 430/128; 702/41; 702/101
(58) Field of Search ......................... 702/41, 42, 101; 72/60; 73/777, 789; 700/45, 98; 430/56, 58.05, 128, 133; 385/128

(56) References Cited

U.S. PATENT DOCUMENTS 5,166,892 A  * 11/1992 Inoue et al. ................. 702/101
5,288,584 A  *  2/1994 Yu .............................. 430/128
6,539,314 B1 *  3/2003 Ondrus et al. ................ 702/41

OTHER PUBLICATIONS

Chien et al., "All fiber polarization mode dispersion compensator", Pub. No.: US 2002/0168165 A1, Provisional application No. 60/276,809, filed on Mar. 15, 2001.*
John S. Horvath, "Mathematical Modeling of the Stress–Strain–Time Behavior of Geosynthetics Using the Findley Equation", Manhattan College Research Report No. CE/GE–98–3, May 1998.*

* cited by examiner

Primary Examiner—John Barlow
Assistant Examiner—John Le
(74) Attorney, Agent, or Firm—Joseph C. Gil; Aron Preis (57) ABSTRACT

The relationship between the stress σ and the strain ε is firstly established in step 100 with short-term tests as a function of the temperature T. In steps 101 to 104, a Findley model is extended in such a way as to obtain a relationship between the strain ε and the stress σ as a function of the time t and the temperature T. The two models are combined in steps 105 and 106, so as to obtain overall a relationship between the stress σ and the strain ε as a function of the time t and the temperature T.

17 Claims, 9 Drawing Sheets

$$\varepsilon_0 = \frac{\sigma}{E}$$

Fig.3

$$\varepsilon_{app}(t) = \varepsilon_0 + m(t/t_0)^n$$

```
┌─────────────────────────────────────────────────────────────┐
│ Establishing the coefficients C₁ to C₁₃ by short-term tests for │ 100
│         σ(T,ε) = A₁ + A₂ + A₃ + + A₄                         │
└─────────────────────────────────────────────────────────────┘
                              │
┌─────────────────────────────────────────────────────────────┐
│ Establishing the coefficients m, n as a funnction of the stress for │
│ different temperatures T₁, T₂, T₃ .... by creep tests:      │ 101
│                              n(σ)                           │
│       ε(t,σ) = σ/E + m(σ)(t/t₀₀)                            │
└─────────────────────────────────────────────────────────────┘
                              │
┌─────────────────────────────────────────────────────────────┐
│ Establishing a respective stress-dependent pprofile m(σ) and n(σ) for │ 102
│ each of the relevant temperaturess T₁, T₂, T₃...            │
└─────────────────────────────────────────────────────────────┘
                              │
┌─────────────────────────────────────────────────────────────┐
│ Establishing the coefficients a₁, a₂, b₀, b₁, , b₂ respectively for the │
│ different temperatures T₁, T₂, , T₃ ... for                 │
│                                                             │
│       m(σ) = a₁·sinh (σ / (σ₀·a₂))                          │ 103
│                                                             │
│       n(σ) = b₀ + b₁(σ/σ₀) + b₂((σ/σ₀))²                    │
└─────────────────────────────────────────────────────────────┘
                              │
┌─────────────────────────────────────────────────────────────┐
│ Establishing functions a₁=f₁(T); a₂=f₂(T); b₀=f₃(T); b₁=f₄(T); b₂=f₅(T) │ 104
└─────────────────────────────────────────────────────────────┘
                              │
┌─────────────────────────────────────────────────────────────┐
│ Establishing E(T) for small ε from σ(T,ε)=A₁+A₂+A₃+A₄=E(T)·ε │ 105
└─────────────────────────────────────────────────────────────┘
                              │
┌─────────────────────────────────────────────────────────────┐
│                                    n(σ,T)                   │
│ Curve family  ε(t,σ,T) = σ/E(T) + m(σ,T)(t/t₀₃)             │ 106
└─────────────────────────────────────────────────────────────┘
```

METHOD AND COMPUTER SYSTEM FOR ESTABLISHING A RELATIONSHIP BETWEEN A STRESS AND A STRAIN

FIELD OF THE INVENTION

The invention relates to a method for establishing a relationship between a stress σ and a strain ε and more particularly to a computer system useful therefor.

SUMMARY OF THE INVENTION

A method is disclosed comprising first establishing the relationship between the stress σ and the strain ε is firstly established in step 100 with short-term tests as a function of temperature T. In steps 101 to 104, a Findley model is extended to obtain a relationship between strain ε and stress σ as a function of time t and temperature T. The two models are combined in steps 105 and 106, to obtain a relationship between the stress σ and the strain ε as a function of the time t and the temperature T.

BACKGROUND OF THE INVENTION

From the prior art, it is known for the relationship between the forces acting in the short term and displacements resulting therefrom to be represented by stress/strain curves. Especially in the field of plastics, such stress/strain curves form an important basis for the design of plastic parts.

The disadvantage with known stress/strain curves is that, because of the large number of tensile tests which are needed, establishing them as a function of temperature is very intensive in terms of time and cost. Furthermore, the known stress/strain curves provide only the relationship between the stress and the strain in short-term tensile tests for the measured temperatures. The profile of the strain as a function of constant loading, depending on its loading time, cannot be established from such stress/strain curves.

The time-dependent inelastic strain component is established in so-called creep tests, in which a constant stress is applied to a sample body for a prolonged time. The disadvantage with this is the periods of time which the creep tests need in order to investigate long-term strain behavior, e.g. after 5, 7, 10 or more years. This data is also a very important basis for the design of plastic parts, but it is often unavailable, or not available with the required accuracy, because of the time taken to carry out the corresponding creep tests.

DETAILED DESCRIPTION OF THE INVENTION

The object of the invention is therefore to provide an improved method, computer system and computer program product for establishing a relationship between the strain and the stress, time and temperature.

The invention makes it possible to establish a relationship between the stress and the strain as a function of the stress loading time, the level of the stress and also the temperature. The task involved with the tensile tests needed for establishing the corresponding coefficients is in this case minimal.

For example, the extrapolation method according to the invention makes it possible, with a relatively short test time of approximately seven weeks, to obtain information about the material behavior for a loading period of more than one year. This applies both to reinforced thermoplastics and to unreinforced thermoplastics, as well as to other plastic materials.

After required coefficients have been established by means of the extrapolation method according to the invention, the resulting function may be used to describe arbitrary stress/strain curves as a function of the loading time t and the temperature T. Such a function may be implemented in a computer program so that a desired curve profile, or a strain or stress value to be calculated, may be obtained at any time by means of a data processing device, for example a personal computer.

This is advantageous for the design of plastic parts, in particular, and permits configuration of the plastic parts while also taking the stress-strain time/temperature behavior into account, and especially with respect to long-term strain behavior.

DESCRIPTION OF THE FIGURES

Figure 1:
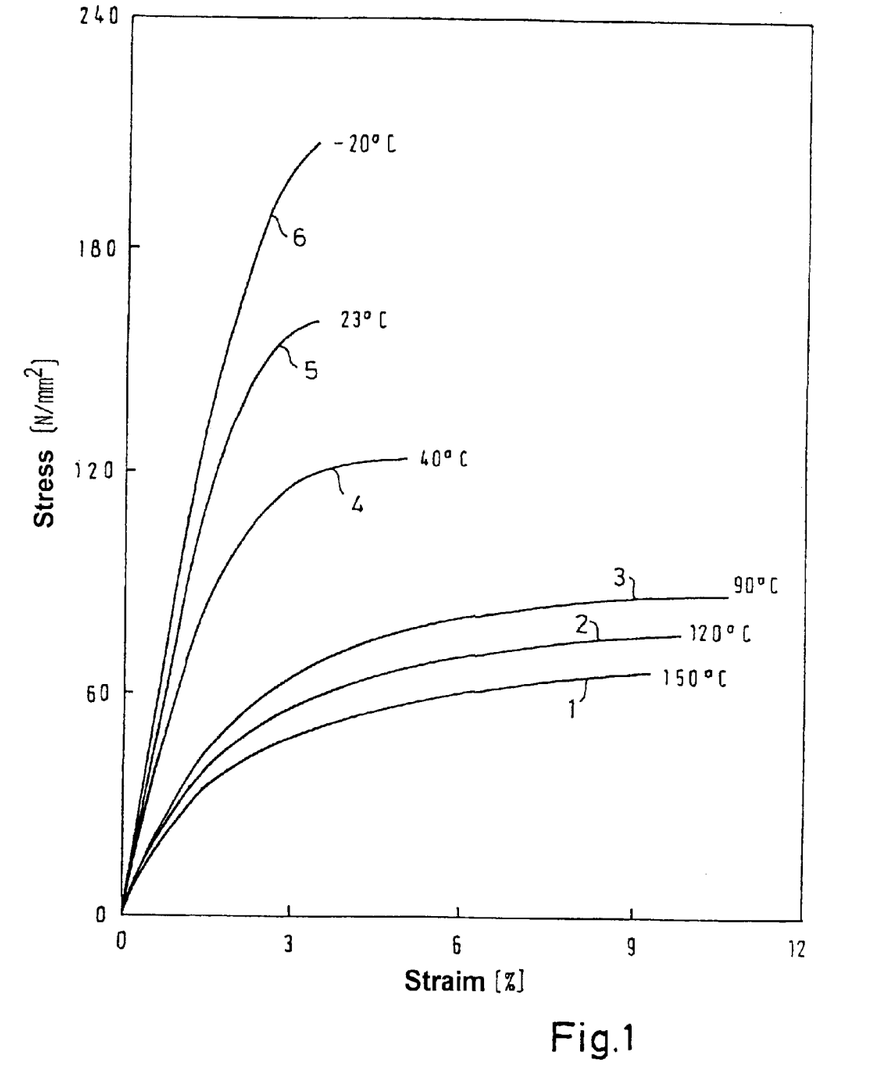
FIG. 1 shows a curve family of stress/strain curves for different temperatures under short-term tensile loading.

An exemplary embodiment of the invention will be explained in more detail below with the aid of the figures, in which:

FIG. 1 shows a family of stress/strain curves 1 to 6. The curves were respectively measured for the material Durethan-BKV 130 (polyamide modified with glass fibre and rubber) with a 4 mm-thick tensile rod in a tensile test at a tensile rate of 5 mm per minute in the freshly injected state.

The stress/strain curve 1 was measured at a temperature of 150° C.; the other stress/strain curves 2 to 6 were measured at temperatures of 120° C., 90° C., 40° C., 23° C. and −20° C., respectively. A calculation using the method according to the invention also gives the same curves. To describe the relationship between the stress σ and the strain ε as a function of the temperature T under short-term tensile loading—as represented in FIG. 1—the following model is in this case selected:

$$\sigma(T,\epsilon) = A_1 + A_2 + A_3 + A_4$$

wherein $$A_1 = c_1\epsilon + c_2\epsilon^3 + c_3\epsilon^5 + c_4\ln(\epsilon + \sqrt{\epsilon^2+1}) \quad (2)$$

$$A_2 = c_5\epsilon T + c_6\epsilon T^3 + c_7\epsilon T^5 \quad (3)$$

$$A_3 = c_8\epsilon^3 T + c_9\epsilon^3 T^3 + c_{10}\epsilon^3 T^5 \quad (4)$$

$$A_4 = c_{11}\epsilon^5 T + c_{12}\epsilon^5 T^3 + c_{13}\epsilon^5 T^5 \quad (5)$$

To determine the coefficients $c_1$ to $c_{13}$, for example from five to ten, preferably from five to seven, short-term tensile tests are in this case carried out at different temperatures for a specific material. On the basis of the experimentally established stress/strain curves, the system of equations resulting therefrom is solved numerically so as to obtain the values of the coefficients $c_1$ to $c_{13}$.

Hence, equation (1) parameterised in this way then describes the relationship between the stress $\sigma$ and the strain $\epsilon$ for arbitrary temperatures T for a specific material under short-term tensile loading.

The corresponding calculated curve profiles are likewise represented in FIG. 1; in the exemplary embodiment in question, the calculated and measured curves are substantially congruous. Discrepancies of the measured curves from the calculated curves can, however, occur in the scope of tolerances due to the measurement and the material.

The creep behavior of the material in the creep test is described by a Findley power function:

$$\varepsilon(t) = \frac{\sigma}{E} + m\left(\frac{t}{t_0}\right)^n \quad (6)$$

wherein $t_0$ is a unit time and m and n involve the so-called creep parameters. Equation (6) hence contains both the elastic strain component and also the viscoelastic and viscous strain component, which is conditioned by the unit time $t_0$ and the creep parameters m and n, as well as the Young's modulus E.

Figure 2:
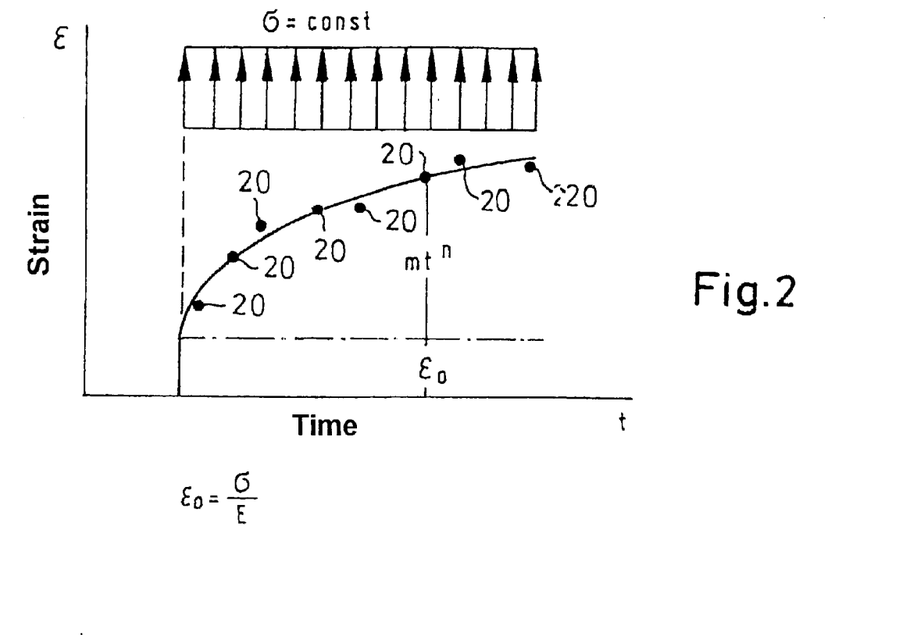
FIG. 2 shows a schematic representation of a Findley power function for a creep test.

FIG. 2 schematically shows the principle of a creep test. In this case, a time-invariant load is applied to a sample body, for example by suspending a defined weight from the sample body. At different times, measurement points 20 are established in order to establish the strain $\sigma$ respectively existing at the time in question.

Figure 3:
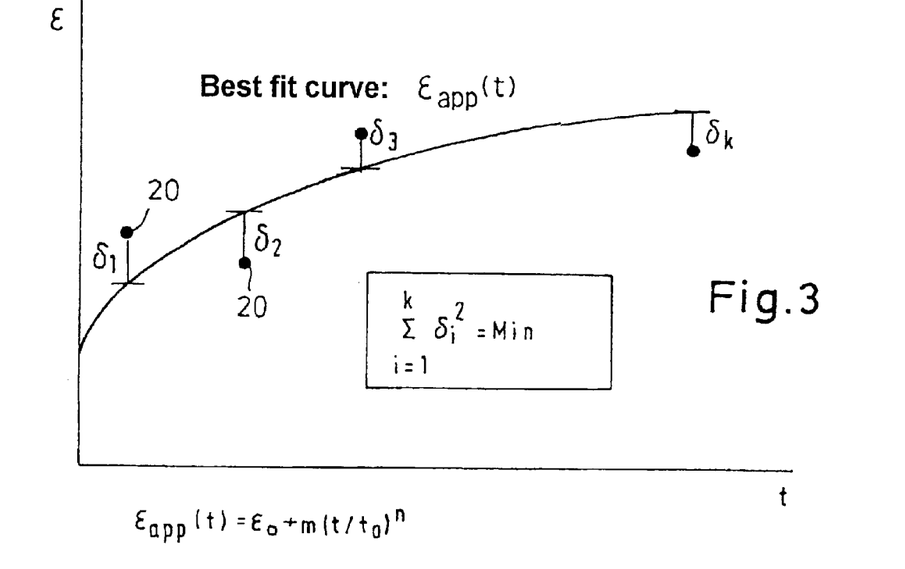
FIG. 3 shows the way in which an approximated curve profile is established for the strain as a function of time for the Findley power function.

FIG. 3 illustrates the way in which the creep parameters m and n are established from the established measurement points 20 using the method of least squares. In this case, the discrepancies $\delta_1$ to $\delta_k$ of the measurement points 20 from an approximated strain curve $\epsilon_{app}(t)$ are employed for establishing the creep parameters m and n.

The creep parameters m and n established in this way then describe the strain profile as a function of time for a specific stress $\sigma$ and at a specific temperature T. The approximated strain curve may also be extrapolated for long loading time scales.

In order to obtain a more general expression for equation (6), the creep parameters m and n are respectively written as a function of the stress $\sigma$:

$$\varepsilon(t,\sigma) = \frac{\sigma}{E} + m(\sigma)\left(\frac{t}{t_0}\right)^{n(\sigma)} \quad (7)$$

Figure 4:
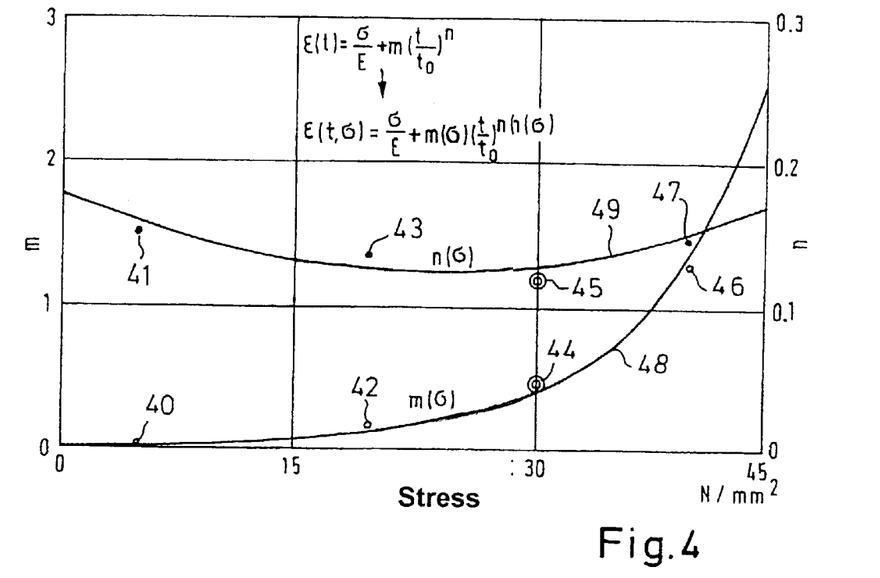
FIG. 4 shows the profile of the coefficients n(σ) and m(σ) as a function of the stress in the creep test for a specific temperature.

Creep tests with a different constant stress $\sigma$ are carried out, in each case for the same temperature, and the creep parameters m and n are established for the different stresses $\sigma$. FIG. 4 shows a result of such a measurement series. The measurement series were in this case carried out at constant temperature T.

Curve 48 indicates the stress-dependent profile of the creep parameter m; curve 49 indicates the stress-dependent profile of the creep parameter n. Curves 48 and 49 are established from the value pairs established for n and m from individual creep tests for different stresses. For example, a creep test is carried out with a stress of approximately 5 Newtons per mm$^2$, the parameter value point 41 being obtained for n and the parameter value point 40 being obtained for m. Corresponding creep tests are carried out for stresses of approximately 20 Newtons per mm$^2$, 30 Newtons per mm$^2$ and 40 Newtons per mm$^2$, so that the further value pairs points 42, 43; 44, 45; 46, 47 are obtained for the creep parameters m and n at the different stresses, respectively, as represented in FIG. 4.

Figure 5:
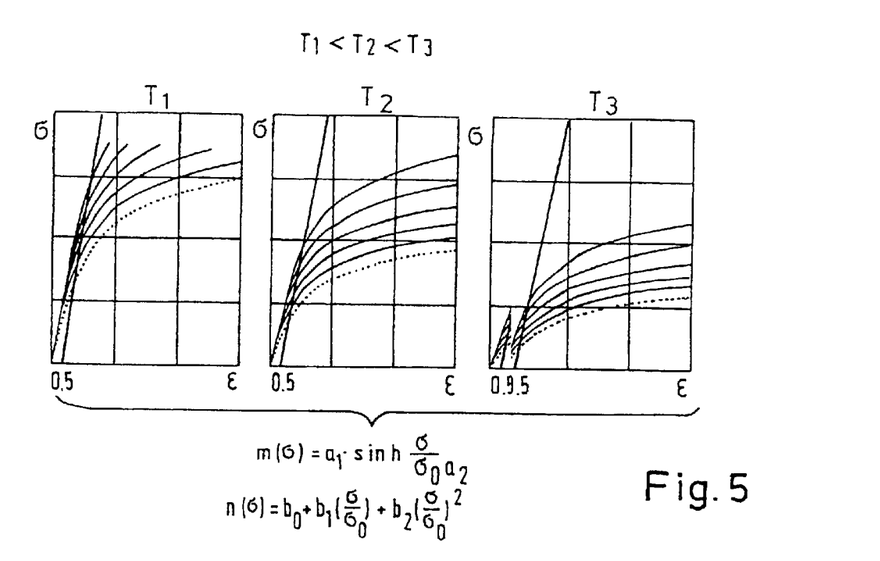
FIG. 5 shows the functions used to approximate the stress-dependent profiles of the coefficients m and n, and the way in which the coefficients of these functions are established, respectively for a specific temperature $T_1$, $T_2$ and $T_3$.

Corresponding creep tests at different stresses a are carried out, for example, at three different temperatures $T_1$, $T_2$ and $T_3$, as represented in FIG. 5. For each of the temperatures $T_1$, $T_2$ and $T_3$, curve profiles of the creep parameters m and n are then established analogously with the curves 47 and 48 in FIG. 4.

The profiles of the creep parameters m and n are furthermore approximated by the following models:

$$m(\sigma) = a_1 \cdot \sinh\frac{\sigma}{\sigma_0 \cdot a_2} \quad (8)$$

$$n(\sigma) = b_0 + b_1\left(\frac{\sigma}{\sigma_0}\right) + b_2\left(\frac{\sigma}{\sigma_0}\right)^2 \quad (9)$$

wherein $a_1$, $a_2$, and $b_0$, $b_1$ and $b_2$, respectively, involve parameter values dependent on the temperature T.

Figure 6:
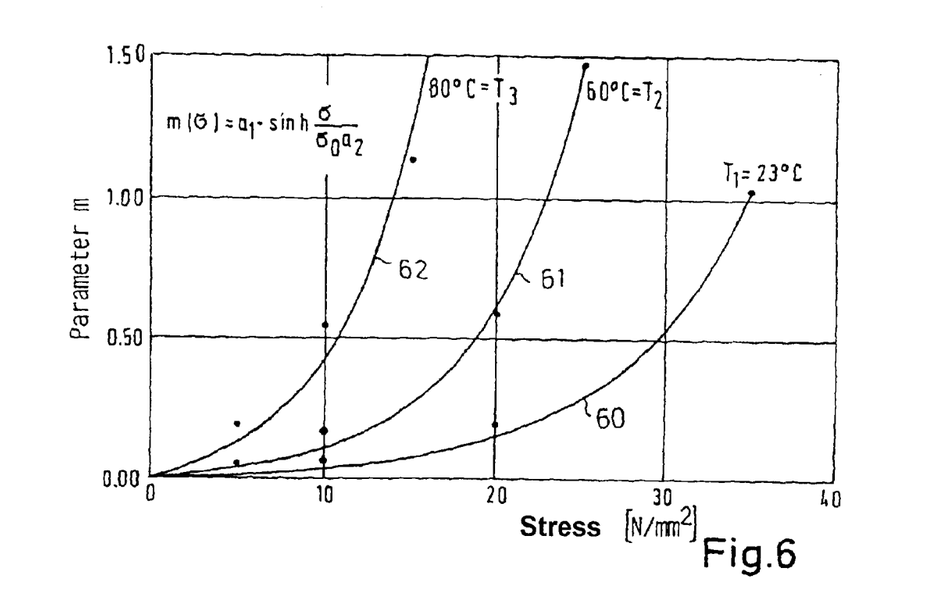
FIG. 6 shows the profile of the coefficient m(σ) for three different temperatures.

FIG. 6 shows three different profiles of the creep parameter m as a function of the stress for three different temperatures, $T_1=23°$ C., $T_2=60°$ C. and $T_3=80°$ C., from which the curve profiles 60, 61 and 62 are obtained.

Figure 7:
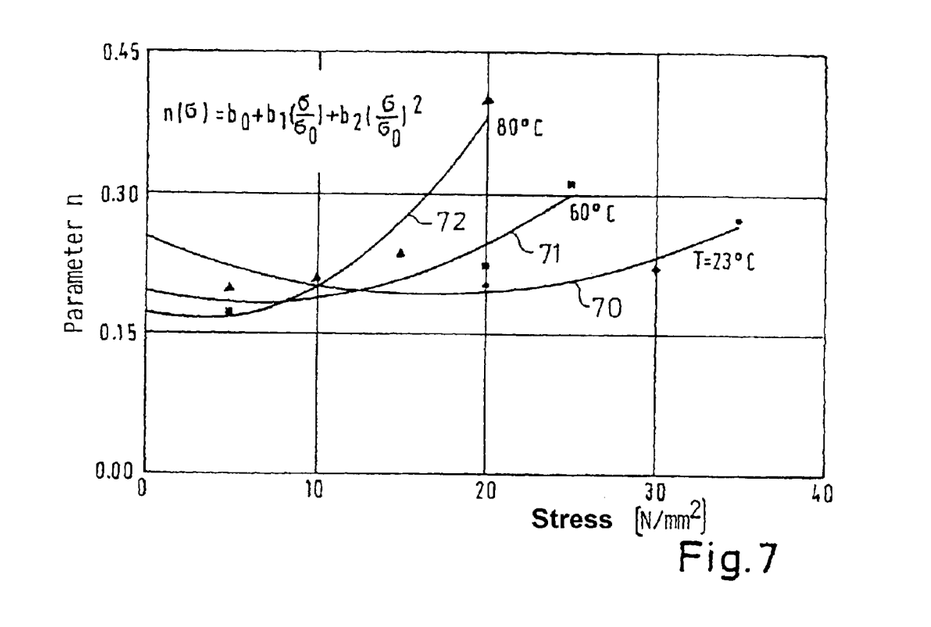
FIG. 7 shows the profile of the coefficient n(σ) for three different temperatures.

FIG. 7 shows the corresponding curves 70, 71 and 72 of the creep parameter n, respectively for a specific temperature, as a function of the stress.

In order to establish curves 60, 61 and 62, and 70, 71 and 72, respectively, the values of the coefficients $a_1$, $a_2$, and $b_0$, $b_1$ and $b_2$, respectively, of formulae (8) and (9) are in each case established on the basis of the individual values established respectively for the creep parameters m and n from the creep tests. The corresponding individual values are also represented in FIGS. 6 and 7.

Figure 8:
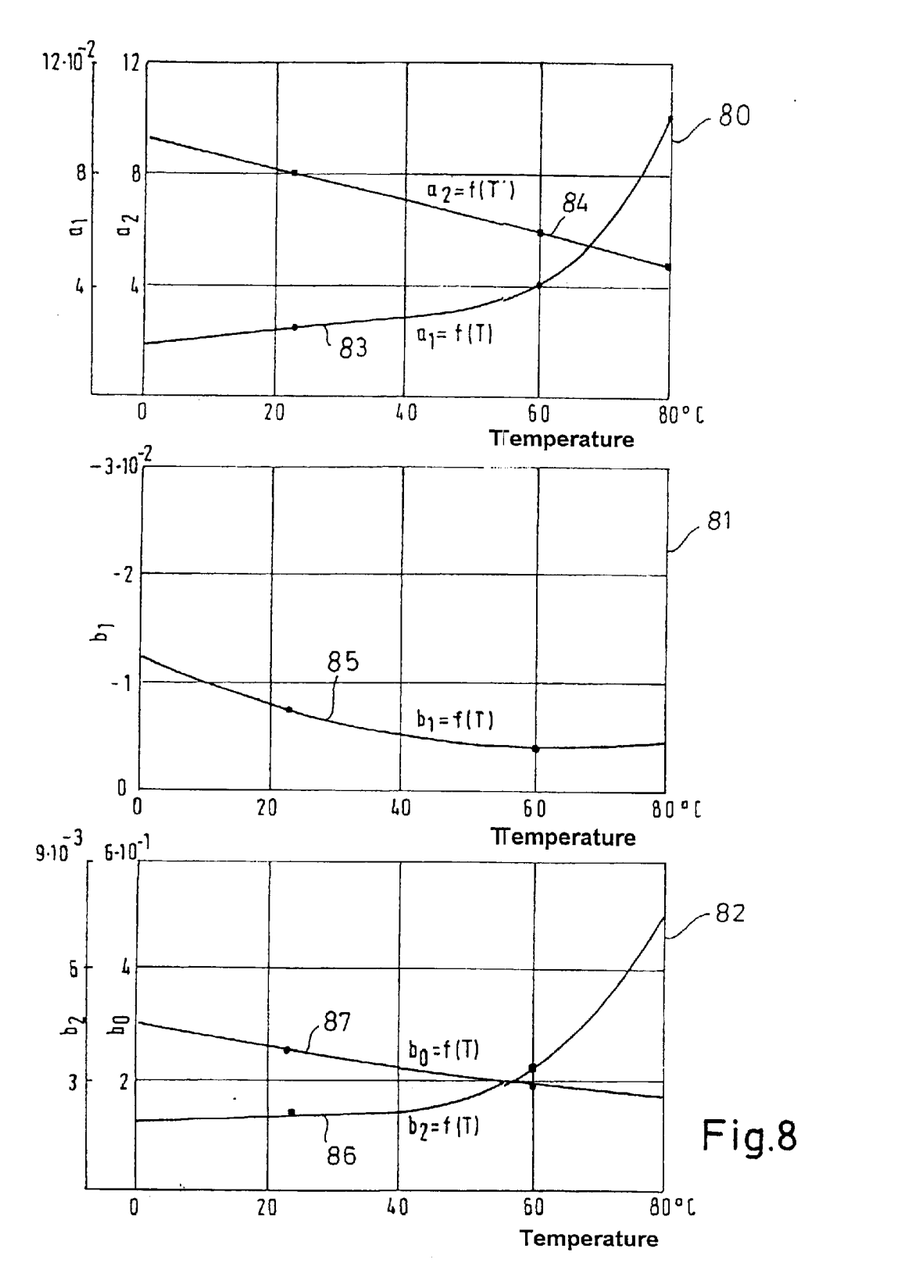
FIG. 8 shows the temperature-dependent profiles of the coefficients $a_1$, $a_2$ as well as $b_0$, $b_1$ and $b_2$ obtained from the profiles n(σ) and m(σ)

FIG. 8 shows the diagrams 80, 81 and 82. Diagram 80 illustrates the profile of the parameters $a_1$, and $a_2$ as a function of the temperature. The corresponding curves 83 and 84 are established on the basis of the values for $a_1$ and $a_2$ established for the temperatures $T_1$, $T_2$ and $T_3$, for example by fitting a polynomial, for instance a spline polynomial, through the points that have been established.

Correspondingly, diagram 81 shows the curve profile 85 for the parameter $b_1$ as a function of the temperatures, curve 85 having in turn been established on the basis of the parameter values established at the temperatures $T_1$, $T_2$ and $T_3$. Here as well, it is again possible to use a polynomial, for instance a spline polynomial, in order to describe the curve 85.

Diagram 82 shows the corresponding curves 86 and 87 for the corresponding profiles of the coefficients $b_0$ and $b_2$.

Figure 9:
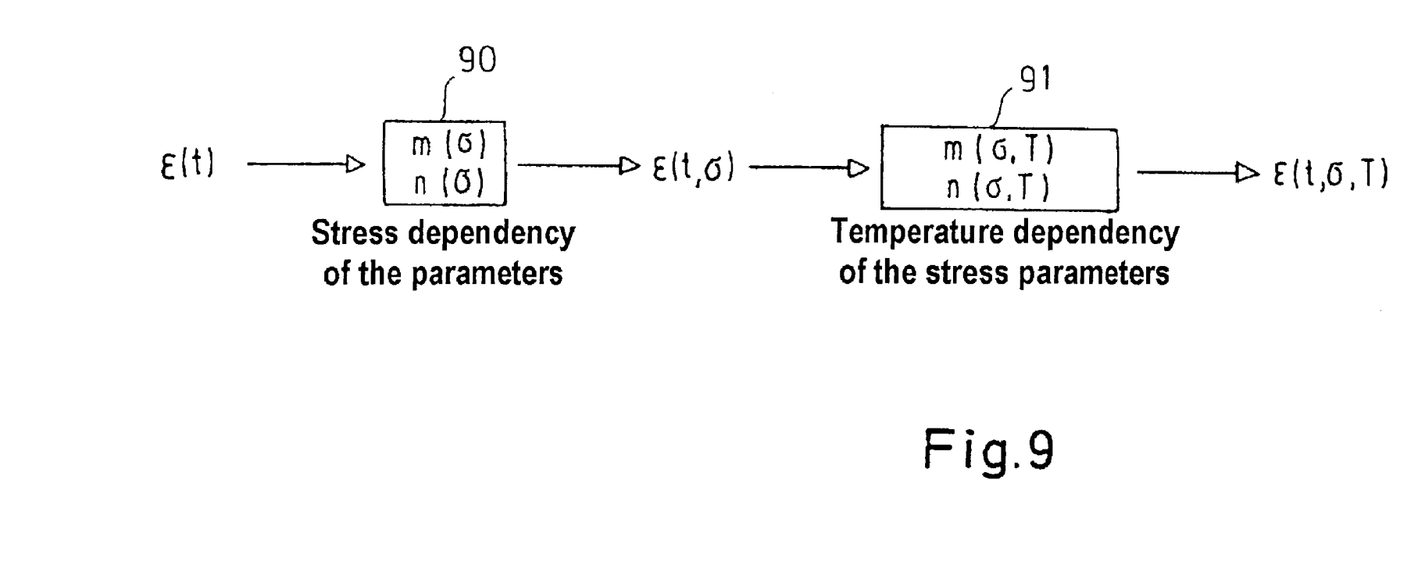
FIG. 9 shows the steps required to establish the stress/strain curve family as a function of the temperature and the stress loading time.

FIG. 9 illustrates the stepwise extension of the Findley model according to a formula (6), which is only time-dependent to a relationship as a function of the time t, the stress c and the temperature T.

To that end, in step 90, the creep parameters m and n are firstly expressed respectively as a function of the stress σ, so that equation (7) is obtained. In the next step 91, the creep parameters m and n are also expressed as a function of the temperature T by introducing the temperature-dependent parameters $a_1$, $a_2$, and $b_0$, $b_1$ and $b_2$, according to formulae (8) and (9). This then finally gives the following relationship.

$$\varepsilon(t, \sigma, T) = \frac{\sigma}{E(T)} + m(\sigma, T)\left(\frac{t}{t_0}\right)^{n(\sigma,T)} \quad (10)$$

Figure 10:
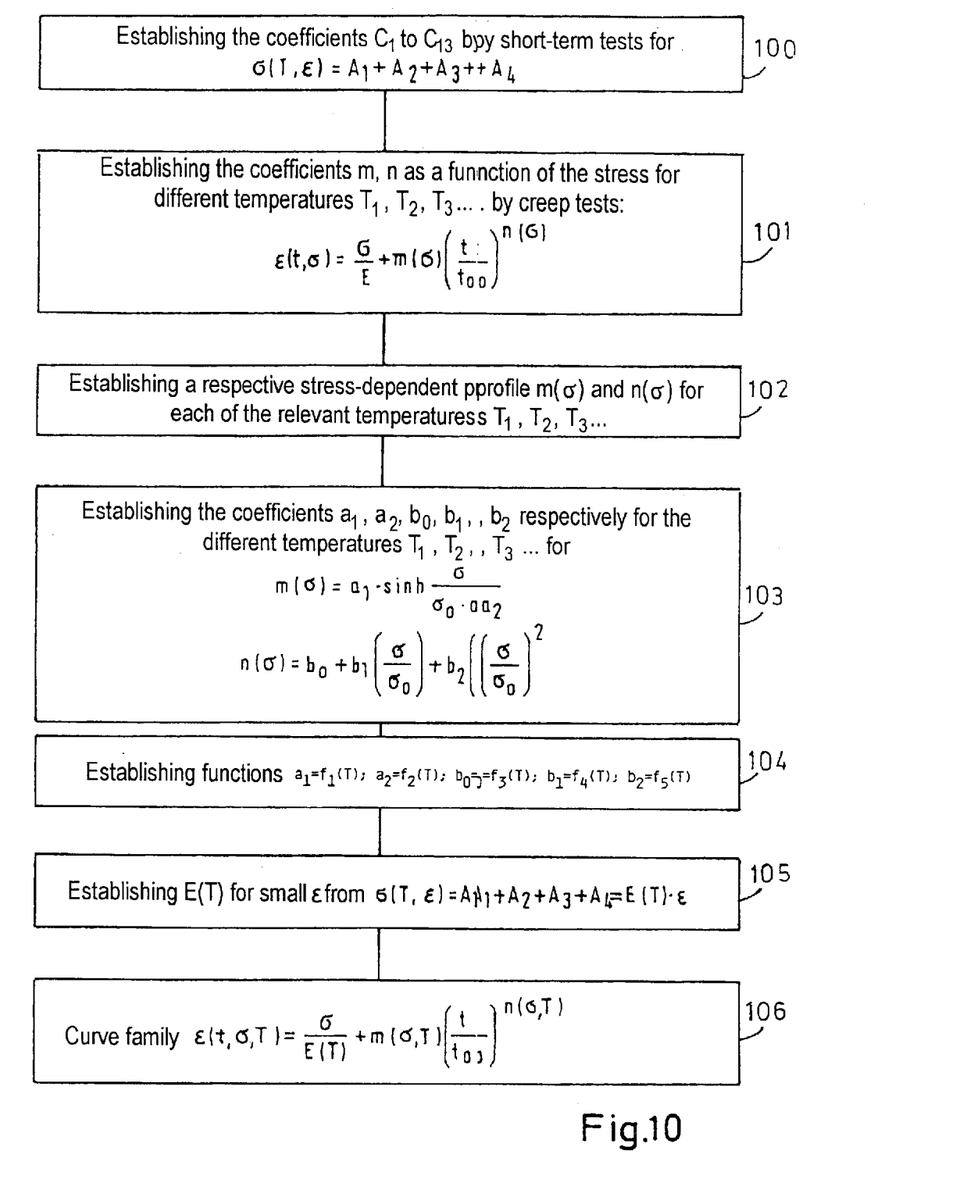
FIG. 10 shows a detailed representation of the steps in FIG. 9 with the aid of a preferred exemplary embodiment.

FIG. 10 shows a flow chart of a method according to the invention for establishing a relationship between the stress σ and the strain ε as a function of the time t and the temperature T. In step 100, for example, the case of short-term loading is firstly investigated by means of short-term tensile tests. The coefficients $c_1$ to $c_{13}$ of the model (1) are thereby established. Hence, the resulting function then describes the relationship between the stress σ and the strain ε as a function of the temperature T under short-term loading.

In step 101, the behavior of the material to be examined is then investigated for the case of long-term loading. To that end, creep tests are respectively carried out for specific temperatures $T_1$, $T_2$ and $T_3$ with different constant stresses σ in each case, and a value pair for the creep parameters n and m is in each case determined from the stress/strain curves that have been established.

This provides, in step 102, a respective stress-dependent profile of the creep parameters m and n as a function of the stress σ for each of the temperatures in question, as is also represented in FIG. 6 and 7 with the aid of an example.

For establishing the creep parameters, it has been found that the invention, for example with a test duration of approximately seven weeks (approximately 1000 h), permits a sufficiently accurate approximation which describes the strain even for loading times of more than one year and longer. This will be explained in more detail with reference to FIGS. 11 and 12.

In step 103, the parameters $a_1$, $a_2$, and $b_0$, $b_1$ and $b_2$, of the models (8) and (9), are established from the experimentally established value points of the stress-dependent profiles of m and n, respectively. From this, corresponding values for the coefficients of the models (8) and (9) are obtained for each of the temperatures in question.

The values of these coefficients are in each case temperature-dependent. To describe the respective temperature relationship, a function f(T) is fitted through the respectively established value points, for example by means of a polynomial or spline-polynomial model. The corresponding polynomials $f_1$ to $f_5$ are established in step 104, analogously with curves 83 to 86 in FIG. 8.

A step 105 establishes the Young's modulus E(T) from formula (1), for example by assuming a relatively small value of between 0.05% and 0.25% for the strain ε, i.e. an extension in the linear Hookean region.

In step 106, the established relationships are then substituted into formula (10), i.e. the relationship E(T) established in step 105 and the relationships for the creep parameters m and n, which are obtained from the models (8) and (9) and the profiles that have been established for the corresponding coefficient values, which are described by the functions $f_1$ and $f_2$ and are dependent on the temperature T.

Formula (10) expressed in this way hence directly indicates a relationship between the stress σ and the strain ε for arbitrary times t and arbitrary temperatures T.

Formula (10) may be implemented by means of a computer program in a data processing system, for example a personal computer, so that a stress/strain curve may be directly calculated and displayed after, for example, a time t of interest and a specific temperature T have been input. By varying the temperature T, for example, the representation in FIG. 1 is then obtained purely computationally.

Figure 11:
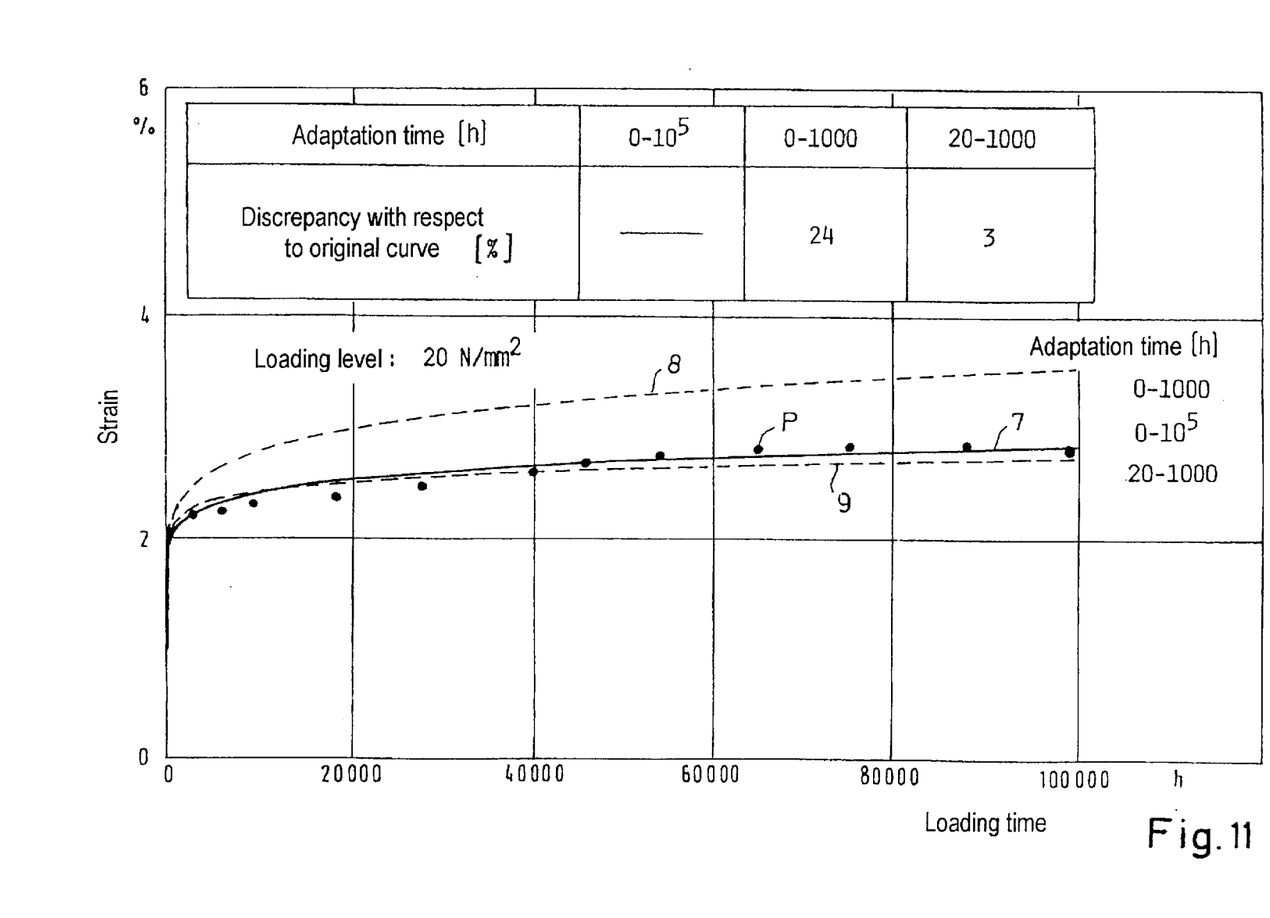
FIG. 11 shows a representation of actual and calculated strain profiles for a creep test.

FIG. 11 shows the strain plotted against the loading time. Curve 7 was established in a creep test with a total loading time of 100,000 hours (approximately 10 years). FIG. 11 furthermore shows the measurement points P on which curve 7 is based.

The dashed curve 8 in FIG. 11 is a curve profile calculated from formula (6), measurement points P for loading times of between t=0 and t=1000 hours having been taken into account for establishing the creep parameters m and n. The dashed curve 9 corresponds to curve 8, but only measurement points between t=20 hours and t=1000 hours were taken into account for calculating the approximation. Omitting the measurement points in the starting region between t=0 and t=20 hours makes curve 9 give a much better approximation than curve 8 does for the curve 7 which was actually measured.

Figure 12:
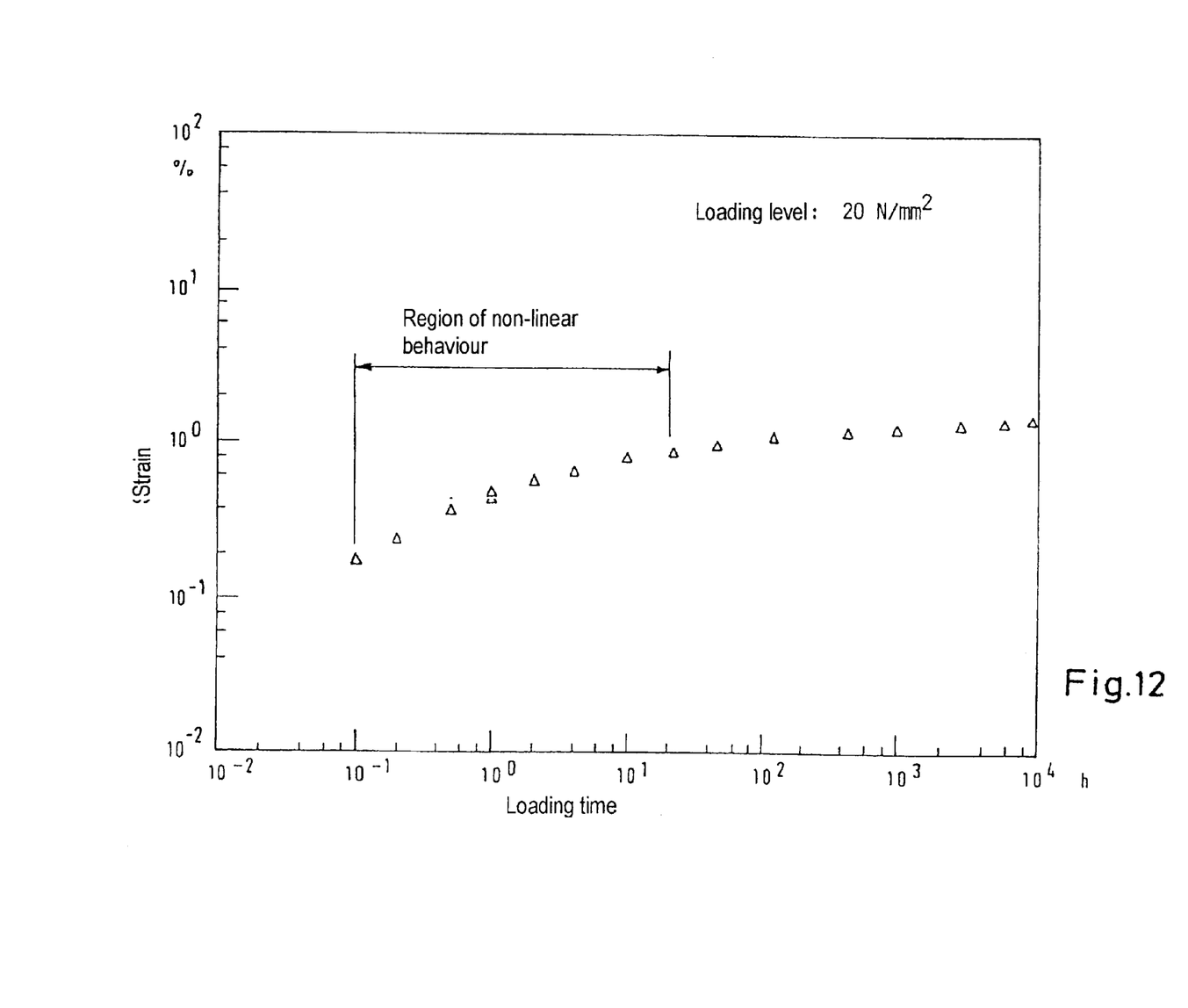
FIG. 12 shows the non-linear starting region of the strain in a creep test, plotted against the loading time.

In general, more accurate extrapolation may be achieved when the measurement values in a starting region up to approximately t=20 to 100 hours are not taken into account for determining the creep parameters m and n. The reason is that the material exhibits a non-linear behavior in the starting region. This is also clarified by FIG. 12:

FIG. 12 shows the strain in % as a function of the loading time for a load of 20 N/mm². It may be seen from the profile of the measurement values in FIG. 12 that the material behavior in the starting region up to approximately 20 hours is non-linear, after which it adopts a linear behavior. To establish the starting region more accurately, the transition between non-linear and linear behavior hence needs to be established.

The method according to the invention for determining the relationship between the stress σ and the strain ε makes it possible to reduce drastically the costs and the time taken for establishing the material properties of plastics. This method furthermore makes it possible, by virtue of the results that are obtained, which are expressed by formula (10), for plastic parts to be designed with greater accuracy, especially as regards the long-term behavior of the material.

The method according to the invention likewise makes it possible to obtain information about the loading limit of the material. Experience of long-term behavior and observations of very many experimental results from tensile creep tests, at room temperature and at elevated temperatures, show that unreinforced thermoplastics reach their dimensional design limit when an inelastic strain of 0.5% is added to the elastic strain. The 0.5% inelastic strain line corresponds to the particular load under which super proportional strain is liable to be recorded within the loading time.

Although the invention has been described in detail in the foregoing for the purpose of illustration, it is to be understood that such detail is solely for that purpose and that variations may be made therein by those skilled in the art without departing from the spirit and scope of the invention except as it may be limited by the claims.

What is claimed is:

1. A method for establishing a relationship between a strain ε and a stress σ as a function of a loading time t of the stress σ and a temperature T, comprising the steps:

(i) determining a first function to describe a relationship between the stress σ and the strain ε as a function of the temperature T, under short-term loading;

(ii) determining a second function to describe a relationship between the strain $\epsilon$ and the stress $\sigma$ as a function of the loading time t, the temperature T and a Young's modulus E(T) dependent on the temperature T, under long-term loading; and (iii) establishing the Young's modulus E(T) as a function of the temperature T from the first function wherein the first function has the following form $$\sigma(T,\epsilon)=A_1+A_2+A_3+A_4$$

wherein $$A_1=c_1\epsilon+c_2\epsilon^3+c_3\epsilon^5+c_4\ln(\epsilon+\sqrt{\epsilon^2+1})$$

$$A_2=c_5\epsilon T+c_6\epsilon T^3+c_7\epsilon T^5$$

$$A_3=c_8\epsilon^3 T+c_9\epsilon^3 T^3+c_{10}\epsilon^3 T^5$$

and $$A_4=c_{11}\epsilon^5 T+c_{12}\epsilon^5 T^3+c_{13}\epsilon^5 T^5.$$

2. The method according to claim 1 wherein the second function involves a Findley power function.

3. The method according to claim 1 in which the second function has the following form:

$$\varepsilon(t,\sigma) = \frac{\sigma}{E} + m(\sigma)\left(\frac{t}{t_0}\right)^{n(\sigma)}$$

wherein m($\sigma$) involves a first stress-dependent coefficient and n($\sigma$) involves a second stress-dependent coefficient.

4. The method according to claim 1 wherein the first function is used to establish the Young's modulus E dependent on the temperature T.

5. The method according to claim 1 in which the established family of curves is described by the following function:

$$\varepsilon(t,\sigma,T) = \frac{\sigma}{E(T)} + m(\sigma,T)\left(\frac{t}{t_0}\right)^{n(\sigma,T)}.$$

6. A computer program product on a computer-readable medium for implementing the method of claim 1 when the program is run on the computer.

7. A data processing program to be run in a data processing system, comprising software components for carrying out the method of claim 1 in a data processing system.

8. A data processing system having means designed to carry out the steps of a method according to claim 1.

9. A method for establishing a relationship between a strain $\epsilon$ and a stress $\sigma$ as a function of a loading time t of the stress $\sigma$ and a temperature T, comprising the steps:

(a) determining a first function to describe a relationship between the stress $\sigma$ and the strain $\epsilon$ as a function of the temperature T, under short-term loading;

(b) determining a second function to describe a relationship between the strain $\epsilon$ and the stress $\sigma$ as a function of the loading time t, the temperature T and a Young's modulus E(T) dependent on the temperature T, under long-term loading; and (c) establishing the Young's modulus E(T) as a function of the temperature T from the first function wherein the first function has the following form $$\sigma(T,\epsilon)=A_1+A_2+A_3+A_4$$

wherein $$A_1=c_1\epsilon+c_2\epsilon^3+c_3\epsilon^5+c_4\ln(\epsilon+\sqrt{\epsilon^2+1})$$

$$A_2=c_5\epsilon T+c_6\epsilon T^3+c_7\epsilon T^5$$

$$A_3=c_8\epsilon^3 T+c_9\epsilon^3 T^3+c_{10}\epsilon^3 T^5$$

$$A_4=c_{11}\epsilon^5 T+c_{12}\epsilon^5 T^3\ c_{13}\epsilon^5 T^5$$

and wherein said second function has the form $$\varepsilon(t,\sigma) = \frac{\sigma}{E} + m(\sigma)\left(\frac{t}{t_0}\right)^{n(\sigma)}$$

wherein m($\sigma$) involves a first stress-dependent coefficient and n($\sigma$) involves a second stress-dependent coefficient wherein the stress-dependent profile of the first coefficient is described by the function $$m(\sigma) = a_1 \cdot \sinh\frac{\sigma}{\sigma_0 \cdot a_2}$$

and the stress-dependent profile of the second coefficient is described by the function $$n(\sigma) = b_0 + b_1\left(\frac{\sigma}{\sigma_0}\right) + b_2\left(\frac{\sigma}{\sigma_0}\right)^2.$$

10. The method according to claim 9 in which a respective stress-dependent profile of the first coefficient and of the second coefficient is established for different temperatures.

11. The method according to claim 10 in which the coefficients of the functions describing the profiles of the stress-dependent first and second coefficients are established from the stress-dependent profiles established for different temperatures.

12. The method according to claim 11 which a further function to describe the temperature dependency of the respective coefficient is established from the coefficients, respectively established for a specific temperature, of the describing the stress-dependent coefficients.

13. The method according to claim 9 wherein the first function is used to establish the Young's modulus E dependent on the temperature T.

14. The method according to claim 9 in which the established family of curves is described by the following function:

$$\varepsilon(t,\sigma,T) = \frac{\sigma}{E(T)} + m(\sigma,T)\left(\frac{t}{t_0}\right)^{n(\sigma,T)}.$$

15. A computer program product on a computer-readable medium for implementing the method of claim 9 when the program is run on the computer.

16. A data processing program to be run in a data processing system, comprising software components for carrying out the method of claim 9 in a data processing system.

17. A data processing system having means designed to carry out the steps of a method according to claim 9.

* * * * *